Dec. 6, 1932. G. B. HART Plant Pat. 48
PLANT OR ROSEBUSH
Filed Jan. 23, 1932
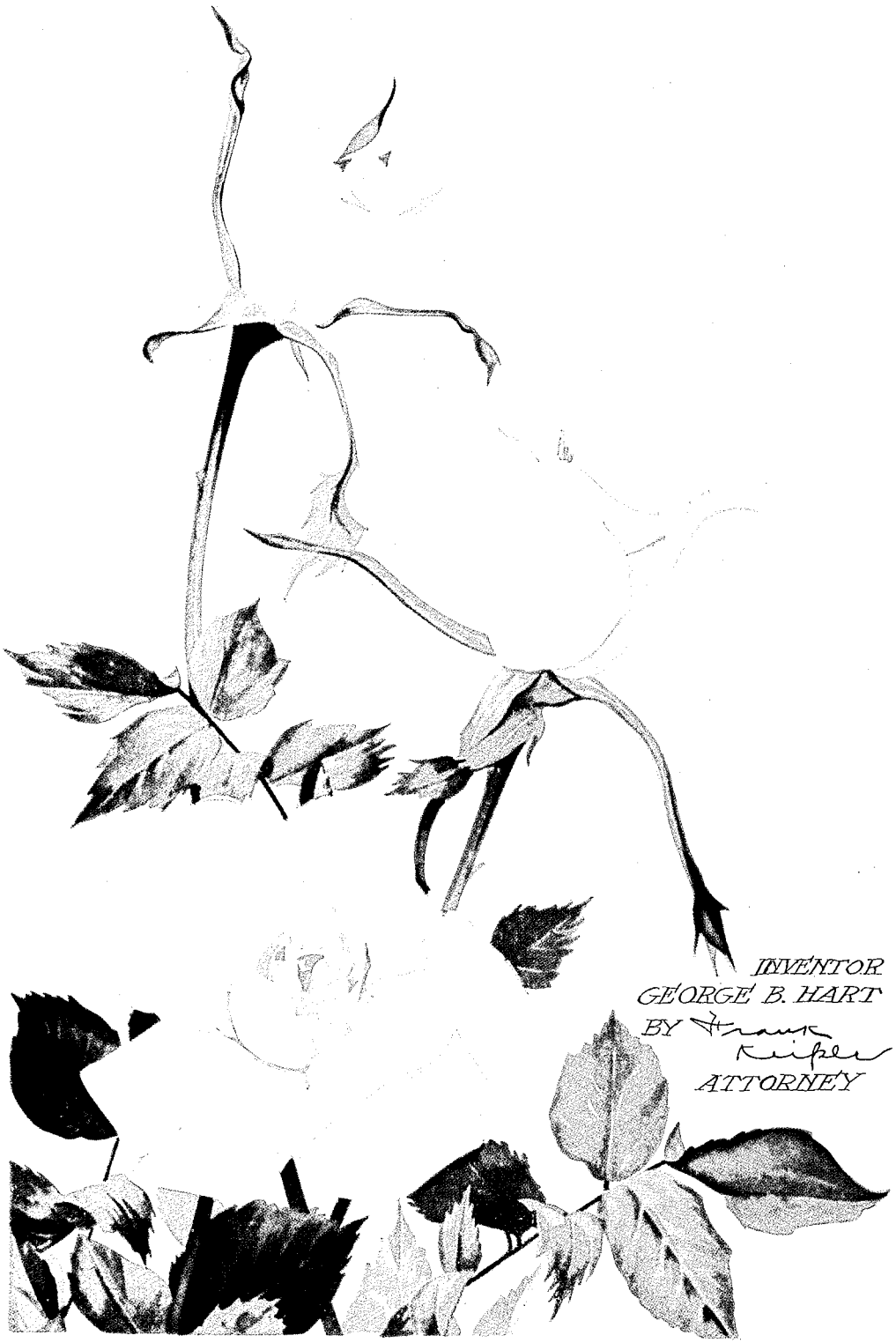

Patented Dec. 6, 1932

Plant Pat. 48

UNITED STATES PATENT OFFICE

GEORGE B. HART, OF BRIGHTON, NEW YORK

PLANT OR ROSEBUSH

Application filed January 23, 1932. Serial No. 588,470.

The object of this invention or discovery is to provide a distinct and new variety of rose and to provide a distinct and new variety of plant producing said rose, said rose having petals of a pink color, as follows. The outside base of the petals is of light cadmium yellow, blending into alizarine pink, the inside of the outer petals being rose color veined with Tyrian rose. The inner petals are eosine pink in color suffused with rose Tyrian. The foregoing colors are those illustrated and described in Ridgeway's color chart, to the colors of which chart reference is made.

This rose, before it opens, is about two and a half times as long, and about two and a half times as large in diameter, as the average Talisman rose. It is a stronger grower than the Talisman rose. The stem is characteristically larger, and diametrically stronger, than is the stem of the Talisman rose. The sepals are longer than the sepals of the Talisman rose, and while they have the characteristic fringed spatulate lobe at the end of the sepals, the lobe is much larger and more pronounced than it is on the sepals of the Talisman rose.

These and other features of the invention or discovery will be illustrated in the drawing, described in the specification, and pointed out in the claim at the end thereof.

In the drawing is shown perspective views of the bud, the half open rose, and the full blown rose, its petals, stem and leaves being shown in natural colors.

This invention or discovery pertains to hybrid tea roses and plants for bearing such roses and has for its object the production of a distinct and new variety of pink hybrid tea rose, the color of the petals of which is as follows:—The outside base of the petals is of light cadmium yellow, blending into alizarine pink, the inside of the outer petals being rose color veined with Tyrian rose. The inner petals are eosine pink in color suffused with rose Tyrian. The foregoing colors are those illustrated and described in Ridgeway's color chart, to the colors of which chart reference is made. The other physical characteristics are as above described.

This rose and the plant bearing it originated as a sport on the Talisman hybrid tea rose, so-called, and has been asexually reproduced as a distinct and new variety of plant, being a hybrid tea rose bush or plant which bears and is capable of bearing pink hybrid tea roses having petals of the shade or color above described.

This rose and the plant bearing it originated as a sport on the Talisman hybrid tea rose, so-called, and has been asexually reproduced by both budding and grafting and the plants or rose bushes so reproduced have borne roses having all of the above characteristics, said roses also having the characteristics, except as to color, of the Talisman hybrid tea rose produced by the Talisman hybrid tea rose plant or bush on which the sport originated which first produced this distinct and new variety of rose and from which sport the distinct and new variety of plants or bushes bearing this distinct and new variety of rose has been asexually propagated or reproduced.

It will also be understood that the distinct and new variety of plant bearing this distinct and new variety of rose is to all outward appearances substantially the same as the plant that regularly bears the so-called Talisman rose.

The serrations of the leaves carry a distinct red tint on the edge, unlike Talisman, which red tint is visible only on close inspection. This tint can be seen as a narrow line around the extreme edge of the face of the leaf, and is shown slightly exaggerated on one leaf of the drawing. This tint appears on the back of the leaf in the midrib, and is suffused through the major part of the under surface. This tint is shown on the lower surface of one of the leaves. The leaf is usually more evenly pigmented on the upper surface than is the Talisman leaf. The arrangement of the veins in the leaves is identical with the Talisman leaf.

The plant generally is the same as the Talisman rose plant, except that the stems are stronger and heavier and the plant is more robust, as is shown in the drawing.

This rose retains its pink color longer than any other pink rose known This is shown by the roses that have been grown up to this time.

I claim—

A new variety of rose bush herein described characterized by having roses in which the outside base of the petals is of light cadmium yellow in color, blending into alizarine pink, the inside of the outer petals being rose colored veined with Tyrian rose and the inner petals being eosine pink in color suffused with rose Tyrian, as shown.

In testimony whereof I affix my signature.

GEORGE B. HART.